United States Patent
Bang et al.

(10) Patent No.: US 9,750,686 B2
(45) Date of Patent: Sep. 5, 2017

(54) LAMINATED FILM AND METHOD FOR LAMINATING FILMS

(71) Applicant: SAMSUNG FINE CHEMICALS CO., LTD., Ulsan (KR)

(72) Inventors: Sung Hwan Bang, Incheon (KR); Kyung Yeol Park, Incheon (KR); Jin Ryul Son, Incheon (KR); Jyung Hee Jeon, Incheon (KR); Ju Hee Shin, Incheon (KR); Sang Youb Lee, Incheon (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 0 days.

(21) Appl. No.: 14/649,430

(22) PCT Filed: Jul. 22, 2013

(86) PCT No.: PCT/KR2013/006521
§ 371 (c)(1),
(2) Date: Jun. 3, 2015

(87) PCT Pub. No.: WO2014/088181
PCT Pub. Date: Jun. 12, 2014

(65) Prior Publication Data
US 2015/0306028 A1    Oct. 29, 2015

(30) Foreign Application Priority Data

Dec. 4, 2012  (KR) .......................... 10-2012-0139847

(51) Int. Cl.
*A61K 9/00* (2006.01)
*A61K 9/70* (2006.01)
(Continued)

(52) U.S. Cl.
CPC ............ *A61K 9/0053* (2013.01); *A61K 9/009* (2013.01); *A61K 9/0065* (2013.01); *A61K 9/70* (2013.01); *A61K 47/38* (2013.01); *B32B 23/20* (2013.01); *B32B 23/22* (2013.01); *B32B 27/08* (2013.01); *B32B 27/18* (2013.01); *B32B 37/00* (2013.01); *B32B 37/0038* (2013.01); *B32B 37/10* (2013.01); *B32B 37/1284* (2013.01); *B32B 37/18* (2013.01); *B32B 2037/1276* (2013.01);
(Continued)

(58) Field of Classification Search
CPC ... B32B 27/08; B32B 37/00; B32B 2307/716; B32B 2317/18; A61K 9/009
See application file for complete search history.

(56) References Cited

U.S. PATENT DOCUMENTS

2011/0014268 A1    1/2011    Tsukioka et al.

FOREIGN PATENT DOCUMENTS

| EP | 2263637 A1 | 12/2010 |
|---|---|---|
| JP | 2000-302694 | 10/2000 |

(Continued)

OTHER PUBLICATIONS

The extended European search report for application No. 13859632.5 dated Jul. 5, 2016.

*Primary Examiner* — Jianfeng Song
(74) *Attorney, Agent, or Firm* — Cantor Colburn LLP (57) ABSTRACT

The inventive concept relates to a laminated film and a method of laminating films, and the disclosed laminated film includes at least two films sequentially stacked and bonded to each other, wherein each of the films may be each independently a gastric film or an enteric film.

5 Claims, 5 Drawing Sheets

(51) Int. Cl.
  *B32B 23/22* (2006.01)
  *B32B 37/12* (2006.01)
  *B32B 37/00* (2006.01)
  *B32B 37/10* (2006.01)
  *B32B 37/18* (2006.01)
  *B32B 23/20* (2006.01)
  *A61K 47/38* (2006.01)
  *B32B 27/08* (2006.01)
  *B32B 27/18* (2006.01)

(52) U.S. Cl.
  CPC ..... *B32B 2307/716* (2013.01); *B32B 2317/18* (2013.01); *B32B 2535/00* (2013.01)

(56) References Cited

FOREIGN PATENT DOCUMENTS

| | | |
|---|---|---|
| JP | 2003-306428 | 10/2003 |
| JP | 2004-339071 | 12/2004 |
| JP | 2007070344 A | 3/2007 |
| JP | 2011143153 A | 7/2011 |
| KR | 1020020062028 | 7/2002 |
| KR | 1020110135630 | 12/2011 |

LAMINATED FILM AND METHOD FOR LAMINATING FILMS

TECHNICAL FIELD

The inventive concept relates to a laminated film and a method of laminating films, and more particularly, to a laminated film including a gastric film and/or an enteric film and method of laminating films.

BACKGROUND ART

Enteric coating techniques used in the medical and functional healthy food fields are used only to facilitate the release of active pharmaceutical ingredients (API) or functional food ingredients entrapped by a coating layer in the intestines, and are mainly performed by using a spray thin layer coating process.

Korean Patent No. 1182827 relates to a method of manufacturing an enteric capsule, deviating an enteric coating technique, by forming a complex including mixing an enteric base material, such as hydroxypropyl methyl cellulose phthalate (HPMCP) and a gastric base material, such as hydroxypropyl methyl cellulose (HPMC) in appropriate proportions. However, the above described technique is also only for a single purpose, that is, to release materials entrapped in a capsule in the intestines.

There is rapidly increased demand from an economic point of view for a technique of transferring a material for oral administration in the medical and functional healthy food fields, that may release at least one material depending on surrounding environmental conditions, have an immediate release property or a sustained release property at a specific pH condition, or be both gastric and enteric properties.

DETAILED DESCRIPTION OF THE INVENTIVE CONCEPT

Technical Problem

The inventive concept provides a laminated film including a gastric film and/or enteric film.

The inventive concept provides a method of laminating films.

Technical Solution

According to an aspect of the inventive concept, there is provided a laminated film including at least two films sequentially stacked and bonded to each other, wherein each of the films may be each independently a gastric film or an enteric film.

The films may all be gastric films.

The films may all be enteric films.

Some of the films may be gastric films, and the others of the films may be enteric films.

The number of the films may be an odd number, and the laminated film may be a film in which the gastric film and enteric film may be alternately laminated.

One side outermost film and the other side outermost film of the films may be both gastric films.

One side outermost film and the other side outermost film of the films may be both enteric films.

The total number of the films may be five.

The gastric film may include at least one selected from a water soluble entrapped material and a poorly water soluble entrapped material, and the enteric film may include a poorly water soluble entrapped material.

The each entrapped material may include at least one selected from an active pharmaceutical ingredient (API) and functional food ingredient.

The enteric film may include an enteric base material, a film forming aid, and a neutralizing agent.

A weight ratio of the film forming aid and the neutralizing agent with respect to the enteric base material may each be in a range of 5:95 to 20:80 and be in a range of 5:100 to 6.5:100, respectively.

The gastric film may include a gastric base material.

A total thickness of the laminated film may be 600 μm or less.

According to another aspect of the inventive concept, there is provided a method of laminating films including bonding at least two films to each other by using an acidic solution as a medium, wherein the films obtain surface adhesiveness when the films contact water.

The method of laminating films may include spraying the acidic solution on a first surface of a first film, disposing a second film on the first surface of the film, and compressing the first film and the second film to each other.

A pH of the acidic solution may be 5.0 or less.

Advantageous Effects

A laminated film according to an exemplary embodiment may be gastric, enteric or both gastric and enteric, and may administer orally a water soluble and/or poorly water soluble material and then release the water soluble and/or poorly water soluble material at a specific pH condition.

BEST MODE

Hereinafter, a laminated film according to an exemplary embodiment will be described in detail.

The laminated film includes at least two films sequentially stacked and bonded to each other.

Each of the films may be each independently a gastric film or an enteric film. The term "gastric film" used herein refers to a film that may dissolve at a pH of gastric juice of pH of about 1.2. The term "enteric film" used herein refers a film that is insoluble in a pH of gastric juice, but dissolves at a pH of enteric juice of pH of about 6.8.

The each film may have a thickness of 120 μm or less.

The gastric film may have an excellent mechanical properties compared to the enteric film.

The enteric film may allow an aqueous medium to permeate therethrough. The aqueous medium used herein refers to water or an aqueous solution.

The films may all be gastric films.

The films may all be enteric films.

Some of the films may be gastric films, and the others of the films may be enteric films.

The number of the films may be an odd number, and the laminated film may be a film in which the gastric film and enteric film may be alternately laminated. In this case, one side outermost film and the other side outermost film of the films may both be gastric films. Alternatively, one side outermost film and the other side outermost film of the films may both be enteric films.

The total number of the films may be five.

The gastric film may include at least one selected from a water soluble entrapped material and a poorly water soluble entrapped material.

The enteric film may include a poorly water soluble entrapped material. The poorly water soluble entrapped material may have a low water solubility, but may have a high bioavailability. In other words, the poorly water soluble entrapped material may not easily dissolve in water, but a body may effectively absorb the poorly water soluble entrapped material when the material is dissolved in non-water components, such as lipid or protein.

The enteric film may include the poorly water soluble entrapped material, and this is related to release mechanisms of the entrapped material in the film: (1) A mechanism that a film itself is dissolved in a solvent to releases an entrapped material in the film. (2) A mechanism that since the film may allow an aqueous medium to permeate therethrough, a water soluble entrapped material is dissolved in the permeated aqueous medium and released, while the aqueous medium is permeating the film. In other words, the enteric film does not dissolve in an aqueous medium at a pH of gastric juice of pH of about 1.2, but still may allow the aqueous medium to permeate therethrough. Accordingly, when the enteric film includes a water soluble entrapped material, the water soluble entrapped material may be pre-released before reaching a small intestine. Thus, in order to prevent the entrapped material from being pre-released, the enteric film may include a poorly water soluble entrapped material. In particular, a particle size of the poorly water soluble entrapped material may be larger than a pore size of the enteric film. Since the poorly water soluble entrapped material has low solubility, the poorly water soluble entrapped material may be prevented from being released, even when the enteric film allowing an aqueous medium to permeate therethrough.

The each entrapped material may include at least one selected from an active pharmaceutical ingredient (API) and functional food ingredient. However, the inventive concept is not limited thereto, and the each entrapped material may include various materials known in the medical and functional healthy food fields.

The API may include a carbamazepine, an ibuprofen, a naproxen, an albendazole, an itraconazole, a dexamethasone, a hydrocortisone, an irbesartan, an olmesartan, an indomethacin, a ketoconazole, an aceclofenac, a celecoxib, a fenofibrate, an imatinib, a clopidogrel, an ofloxacin, a piroxicam, a digoxin, a fluorouracil, or a combination thereof.

The functional food ingredient may include a curcumin, a silymarin, a resveratrol, or a combination thereof.

The enteric film may include an enteric base material, a film forming aid, and a neutralizing agent.

The enteric base material is indissoluble at a pH of gastric juice (pH of about 1.2) at least for 2 hours to 4 hours, but promptly dissolves at a pH of enteric juice (pH of about 6.8) within 10 minutes. The enteric base material may include at least one compound from the group consisting of a hydroxypropyl methyl cellulose phthalate (HPMCP) and a hydroxypropyl methyl cellulose acetate succinate (HPMCAS). Examples of HPMCP include an HPMCP HP-55 that is available from Samsung Fine Chemicals (containing an amount of methoxy group in a range of 18 to 22 wt %, an amount of hydroxypropoxy group in a range of 5 to 9 wt %, and an amount of phthalyl group in a range of 27 to 35 wt %; 200731 Type; and a kinematic viscosity in a range of 32 centistokes (cSt) to 48 cSt. Here, the amount of methoxy group and other substituents in weight percentage are based on a total weight of entire molecules. It is the same hereinafter.), HPMCP HP-55S (containing an amount of methoxy group in a range of 18 to 22 wt %, an amount of hydroxypropoxy group in a range of 5 to 9 wt %, and an amount of phtalyl group in a range of 27 to 35 wt %; 200731 Type; and a kinematic viscosity in a range of 136 cSt to 204 cSt), and HPMCP HP-50 (containing an amount of methoxy group in a range of 20 to 24 wt %, an amount of hydroxypropoxy group in a range of 6 to 10 wt %, and an amount of phtalyl group in a range of 21 to 27 wt %; 220824 Type; and kinematic viscosity in a range of 44 cSt to 66 cSt).

The film forming aid is to increase an elasticity and formability of an enteric film that is brittle, and may include cellulose ether. The cellulose ether may include at least one compound selected from the group consisting of hydroxypropylmethylcellulose (HPMC) and methylcellulose (MC). The HPMC contains an amount of hydroxypropoxy group in a range of 4 to 12 wt %, for example, 4 to 7.5 wt % and an amount of methoxy group in a range of 19 to 30 wt %, for example, 27 to 30 wt %. In addition, a viscosity of the HPMC may be in a range of 3 to 50 centipoise (cps), for example, 3 to 15 cps, based on 2 wt % aqueous solution.

A weight ratio of the film forming aid to the enteric base material may be in a range of 5:95 to 20:80. When an amount of the film forming aid is within this range, the enteric film may have excellent elasticity and film formability, as well as satisfactory enteric functions.

The neutralizing agent that solubilizes the enteric base material may be a basic material, such as sodium hydroxide, aqueous ammonia, potassium hydroxide, and calcium hydroxide.

A weight ratio of the neutralizing agent to the enteric base material may be in a range of 5:100 to 6.5:100. When an amount of the neutralizing agent is within this range, the enteric base material may easily be solubilized during the manufacturing process of the enteric film, and the enteric film may have a good enteric property.

The gastric film may include a gastric base material.

The gastric base material may include cellulose ether. The cellulose ether may include HPMC. The HPMC contains an amount of hydroxypropoxy group in a range of 4 to 12 wt %, for example, 4 to 7.5 wt % and an amount of methoxy group in a range of 19 to 30 wt %, for example, 27 to 30 wt %. In addition, a viscosity of the HPMC may be in a range of 3 to 50 cps, for example, 3 to 15 cps, based on 2 wt % aqueous HPMC solution.

A total thickness of the laminated film may be 600 μm or less. When the total thickness of the laminated film is more than 600 μm, a rate of dissolution of the laminated film in water or an aqueous solution becomes too slow, and thus an absorption rate of the entrapped material decreases, and in the case of oral intake, administration may be difficult due to an excessively large volume of the laminated film.

Hereinafter, a method of laminating films will be described in detail.

(Preparation of Enteric Film Solution)

First, the enteric base material, the film forming aid, and the neutralizing agent may be mixed in an appropriate proportion in order to prepare a premix in the form of powder. Afterward, the premix may be added to water at room temperature (about 25° C.) and mixed so as to dissolve the premix. Then, the poorly water soluble entrapped material may be added to the resultant, and mixed so as to dissolve and/or disperse the entrapped material. Thereafter, the resultant may be left at room temperature to remove foam (bubbles). As a result, a clear enteric film solution may be obtained. Here, a solid content in the enteric film solution may be in a range of 10 to 30 wt %. When a solid content in the enteric film solution is beyond this range, the formation of the film may be difficult.

(Preparation of Gastric Film Solution)

First, a gastric base material may be added to hot water and stirred. Afterward, the resultant may be left at room temperature (about 25° C.) or stored at a refrigeration temperature (about 0 to about 10° C.). During the storage, the gastric base material may gradually dissolve in water and aggregate, and thus, become gelated. In order to prevent this gelation, the contents may be stirred intermittently. Once the gastric base material dissolves in water completely, the water soluble entrapped material and/or poorly water soluble entrapped material may be added to the resultant, and mixed in order to dissolve and/or disperse the entrapped material. Thereafter, the resultant may be left at room temperature (about 25° C.) to remove foam (bubbles). As a result, a clear gastric film solution may be obtained. Here, a solid content in the gastric film solution may be in a range of 10 to 30 wt %. When a solid content in the gastric film solution is beyond this range, the formation of the film may be difficult.

(Preparation of Enteric Film or Gastric Film)

The enteric film solution or the gastric film solution may be coated on a glass substrate by using a film caster. Then, the glass substrate coated with the enteric film solution or the gastric film solution may be dried. Then, the dried film may be separated from the glass substrate in order to obtain an enteric film or a gastric film. Afterward, the enteric film or the gastric film may be cut to an appropriate size as required.

(Film Lamination)

First, at least two films may be bonded to each other by using an acidic solution as a medium. The films may obtain surface adhesiveness when contacting with moisture. For example, the acidic solution may be sprayed on a first surface of the first film. Then, a second film may be disposed on the first surface of the first film.

Then, the first film and the second film may be compressed together.

A pH of the acidic solution may be 5.0 or less. When a pH of the acidic solution is within this range, in the case that the films include an enteric film, a surface of the enteric film may not dissolve in the acidic solution during the film lamination process, thereby preventing the entrapped material (particularly, the poorly water soluble entrapped material) from being pre-released.

The first film and the second film may be each independently an enteric film or a gastric film.

When the laminated film is orally administered, the gastric film may release an entrapped material in a stomach (pH 1.2), the enteric film may pass through the stomach while preserving most of entrapped materials, and the film itself may dissolve (dissociate) in an intestine (pH 6.8), thereby releasing the entrapped materials.

Mode of the Inventive Concept

Hereinafter, the inventive concept will be described in detail with reference to Examples; however, the inventive concept is not limited thereto.

EXAMPLE

Preparation Example 1: Preparation of Enteric Film 90 parts by weight of enteric base material (HPMCP HP-50, available from Samsung Fine Chemicals), 10 parts by weight of film forming aid (HPMC: AnyCoat-C BN4, available from Samsung Fine Chemicals), and a neutralizing agent (NaOH, in an amount of 6.5 parts by weight based on 100 parts by weight of enteric base material) were mixed. Then, 20 parts by weight of the resultant were added to 80 parts by weight of water at room temperature (25° C.), and mixed for about 30 minutes to dissolve the resultant. Then, 2 parts by weight of carbamazepine, which is a poorly water soluble entrapped material, based on 100 parts by weight of total solids of the resultant, was added to the resultant, and then was mixed to homogeneously disperse the resultant. Thereafter, the final resultant was left at room temperature (25° C.) for about a day, thereby obtaining a clear enteric film solution from which bubbles are removed.

The enteric film solution was coated on a glass substrate (24 cm×30 cm) by using a film caster (self-manufactured by Samsung Fine Chemicals). Then, the glass substrate coated with the enteric film solution was dried at 25° C. and 50% relative humidity (RH) condition. Then, the dried film was separated from the glass substrate to obtain an enteric film.

Preparation Example 2: Preparation of Gastric Film 80 parts by weight of hot water (at about 100° C.) were added to 20 parts by weight of gastric base material (HPMC: AnyCoat-C BN4 available from Samsung Fine Chemicals) and stirred for five minutes. Afterward, the resultant was stored at room temperature (at about 25° C.). During the storage, the gastric base material gradually dissolved in water and aggregate, and thus, become gelated. In order to prevent this gelation, the resultant was stirred intermittently. After the gastric base material completely dissolved, 2 parts by weight of carbamazepine, which is a poorly water soluble entrapped material, based on 100 parts by weight of total solids of the resultant, was added to the resultant, then, was mixed to homogeneously disperse the resultant. Thereafter, the resultant was left at room temperature (at 25° C.) for about 12 hours so as to remove bubbles. As a result, a clear gastric film solution was obtained.

The gastric film solution was coated on a glass substrate (24 cm×30 cm) by using a film caster (self-manufactured by Samsung Fine Chemicals). Then, the glass substrate coated with the gastric film solution was dried at 25° C. and 50% RH condition. Then, the dried film was separated from the glass substrate to obtain a gastric film.

Examples 1 to 8: Preparation of a Laminated Film in Which Films are Bonded to Each Other The enteric film prepared in Preparation Example 1 and the gastric film prepared in Preparation Example 2 were cut to a size of 10 mm×20 mm, respectively. Then, the cut enteric film and/or gastric film were laminated to prepare a laminated film, according to Table 1. Here, the film lamination was performed as follows: That is, aqueous hydrochloric acid solution of pH 4.0 was sprayed on a first surface of a first film, and a second film was disposed on the first surface of the first film, and then the resultant was compressed by using a small flat plate compressor. When laminating N number of films, the aqueous hydrochloric acid solution was sprayed on a surface of N−1 number of (laminated) films, an additional film was further disposed on the surface of N−1 number of (laminated) films on which the aqueous hydrochloric acid solution was sprayed, and then, compressing of the entire films was performed repeatedly, thereby preparing N number of laminated films. Here, N was a number from 2 to 5. In addition, when a laminated film in Table 1 includes both an enteric film and gastric film, the enteric film and the gastric film were alternately laminated.

Comparative Examples 1 to 3: Preparing Plurality of Films

In order to use films in a separated form, not being bonded to each other, a plurality of films were prepared as in Table 1.

TABLE 1

| | Number of enteric films | Number of gastric films | Total number of films | Total thickness of laminated film (μm) | Amount of entrapped material in each film (mg) |
|---|---|---|---|---|---|
| Example 1 | 1 | 1 | 2 | 240 | 20 |
| Example 2 | 1 | 2 | 3 | 360 | 30 |
| Example 3 | 2 | 1 | 3 | 360 | 30 |
| Example 4 | 2 | 2 | 4 | 480 | 40 |
| Example 5 | 3 | 2 | 5 | 600 | 50 |
| Example 6 | 2 | 3 | 5 | 600 | 50 |
| Example 7*[1] | 0 | N | N | 240 to 600 | 20 to 50 |
| Example 8*[1] | N | 0 | N | 240 to 600 | 20 to 50 |
| Comparative Example 1*[1] | 0 | N | N | — | 20 to 50 |
| Comparative Example 2*[1] | N | 0 | N | — | 20 to 50 |
| Comparative Example 3 | 2 | 2 | 4 | — | 40 |

*[1]including all cases of N = 2, 3, 4, and 5.

EVALUATION EXAMPLE

Evaluation Example 1: Evaluation of Film Breaking Strength

Figure 1:
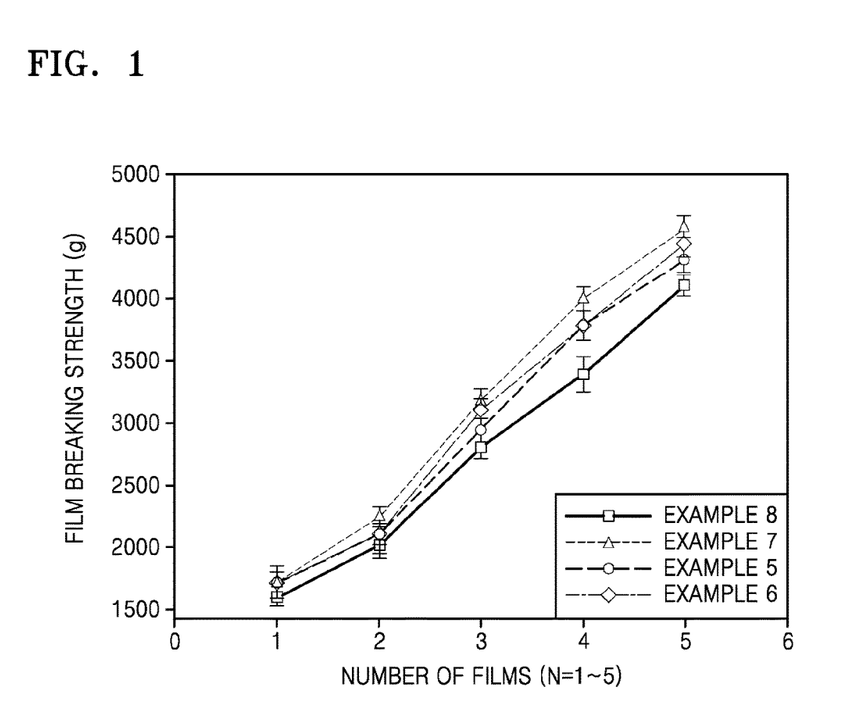
FIG. 1 is a graph showing film breaking strengths depending on the number of films.

Film breaking strengths of the single film (N=1) or laminated films (N=2, 3, 4 or 5) used or prepared in Examples 5 to 8 were measured for the first film. Every time lamination of an additional film was completed, a film breaking strength of the resulting films was measured again. The results thereof are shown in FIG. 1. Here, Brookfield Texture Analyzer CT3 was used as a film breaking strength measuring apparatus, and film breaking strengths were measured ten times for each sample. Average values thereof were recorded as film breaking strengths.

Referring to FIG. 1, it was found that as the number of laminated films increased, and as the proportion of gastric films having excellent mechanical properties in the laminated films increased, the film breaking strengths increased.

Evaluation Example 2: Evaluation of Film Impact Resistance

Figure 2:
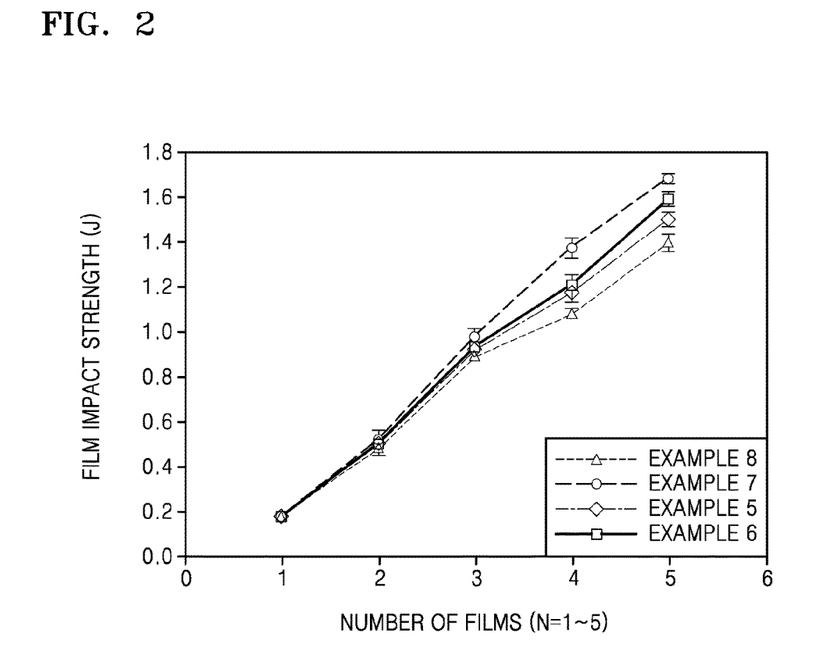
FIG. 2 is a graph showing film impact strengths depending on the number of films.

Film impact resistances of a single film (N=1) or laminated films (N=2, 3, 4 or 5) used or prepared in Examples 5 to 8 were measured for the first film. Every time completing lamination of additional film, film impact resistances of the resulting films were measured again. The results thereof are shown in FIG. 2. Here, FIT-01 Film Pendulum Impact Tester (ASTM D3420) was used as a film impact resistance measuring apparatus, and film impact resistances were measured ten times for each sample. Average values thereof were recorded as film impact resistances.

Referring to FIG. 2, it was found that as the number of laminated films increased, and as the proportion of gastric films having excellent mechanical properties in the laminated films increased, the film impact resistances increased.

Evaluation Example 3: Evaluation of Remaining Rate of Entrapped Materials

Figure 3A:
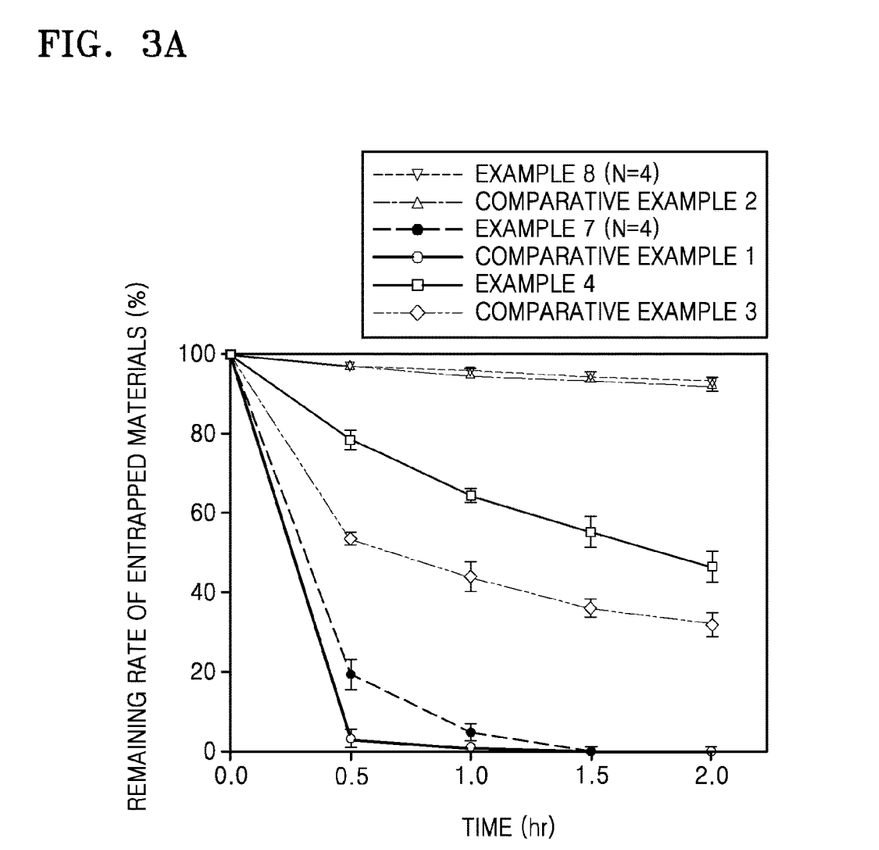
FIG. 3A is a graph showing remaining rates of entrapped materials over time, when immersing laminated films or a plurality of separated films prepared in Examples 4, 7, and 8 and Comparative Examples 1 to 3 in a buffer solution of pH 1.2.

Laminated films prepared in Examples 4, 7, and 8 and a plurality of films prepared in Comparative Examples 1 to 3 were immersed in a buffer solution (aqueous hydrochloric acid solution) of pH 1.2 and a buffer solution (aqueous phosphoric acid solution) of pH 6.8, and remaining rate of entrapped materials in the films were measured, respectively. The results thereof are shown in FIG. 3A (the buffer solution of pH 1.2) and FIG. 3B (the buffer solution of pH 6.8), respectively. Here, a Dissolution Test instrument (Pharmatest PTWS 310) was used as a measuring apparatus of the remaining rate of entrapped materials, and analysis of the remaining rate of entrapped materials were performed following a dissolution test method among general test methods in Korean Pharmacopoeia.

Figure 3B:
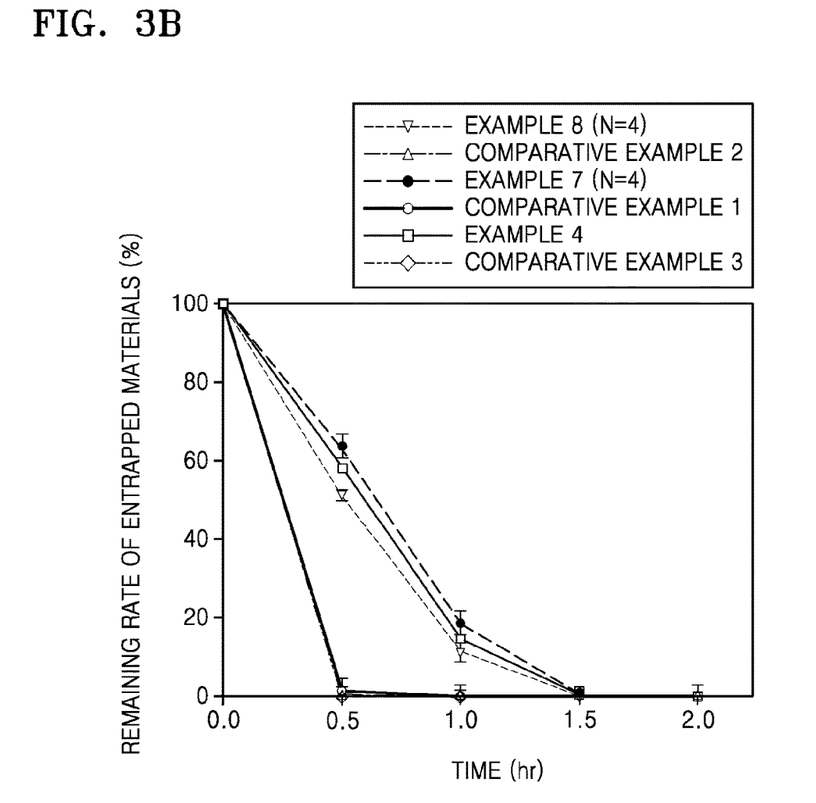
FIG. 3B is a graph showing remaining rates of entrapped materials over time, when immersing laminated films or a plurality of separated films prepared in Examples 4, 7, and 8 and Comparative Examples 1 to 3 in a buffer solution of pH 6.8.

Referring to FIGS. 3A and 3B, it was found that with respect to laminated films prepared in Examples 4, 7, and 8, in which the films are bonded to each other, controlling of the release time of entrapped materials is possible, unlike the plurality of films prepared in Comparative Examples 1 to 3, in which the films are separated from each other. In addition, it was verified that as the proportion of enteric films in the laminated films or the plurality of films separated from each other increased, release of the poorly water soluble entrapped materials in a gastric juice condition of pH 1.2 was suppressed.

Figure 4:
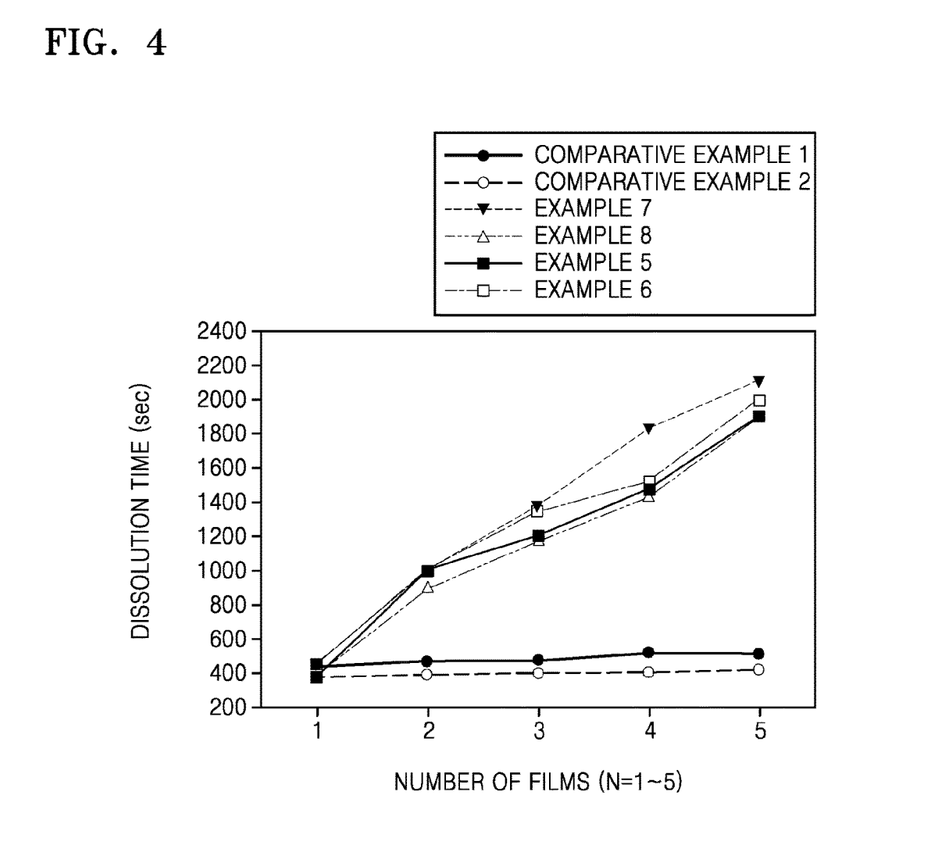
FIG. 4 is a graph showing dissolution times of a film(s) depending on the number of films, when immersing a single film, laminated films or a plurality of films separated from each other in a buffer solution of pH 6.8.

Evaluation Example 4: Evaluation of Dissolution Rate of Laminated Films or Plurality of Films Separated from Each Other A single film (N=1) or laminated films (N=2, 3, 4 or 5) used or prepared in Example 5 to 8 and a single film (N=1) or the plurality of films separated from each other (N=2, 3, 4, or 5) used or prepared in Comparative Examples 1 and 2 were immersed in a buffer solution (aqueous phosphoric acid solution) of pH 6.8 in order to measure film dissolution times. The results thereof are shown in FIG. 4. That is, in each Example and Comparative Example, a single film, double film, triple film, quadruple film, and quintuple film were prepared, and dissolution time of the 5 types of films were measured. The results thereof are shown in FIG. 4. Here, a Disintegration Test instrument (Pharmatest PTZ-E) was used as a film dissolution time measuring apparatus, and film dissolution time was measured at room temperature (at 25° C.) condition. Film dissolution time analysis was performed following a disintegration test method among general test methods in Korean Pharmacopoeia.

Referring to FIG. 4, it was found that laminated films prepared in Examples 5 to 8, in which films are bonded to each other, had longer film dissolution time compared to the plurality of films prepared in Comparative Example 1 and 2, in which films are separated from each other. In addition, as the number of laminated films or the plurality of films separated from each other increased, and as the proportion of gastric films not including neutralizing agent in laminated films or the plurality of films separated from each other increased, film dissolution time increased.

While the inventive concept has been particularly shown and described with reference to exemplary embodiments thereof and the drawings, it will be understood that various changes in form and details may be made therein without departing from the spirit and scope of the following claims.

The invention claimed is:

1. A laminated film comprising:
   at least a gastric film and an enteric film, wherein the gastric film is disposed on and bonded to a surface of the enteric film,
   wherein the gastric film comprises at least one selected from a water soluble entrapped material and a first poorly water soluble entrapped material,
   wherein the enteric film comprises a second poorly water soluble entrapped material,
   wherein the enteric film allows an aqueous medium to permeate therethrough, and
   wherein the first poorly water soluble entrapped material and the second poorly water soluble entrapped material are the same or different,
   wherein the laminated film is prepared by bonding a gastric film and an enteric film to each other by using an acidic solution as a medium, wherein the gastric film and the enteric film obtain surface adhesiveness when the films contact water,
   wherein the bonding comprises
   spraying the acidic solution on a first surface of one of the gastric film and the enteric film,
   disposing the other of the gastric film and the enteric film on the first surface, and
   compressing the gastric film and the enteric film to each other.

2. The laminated film of claim 1, wherein the number of the films is an odd number, and the gastric film and the enteric film are alternately laminated.

3. The laminated film of claim 2, wherein one side outermost film and the other side outermost film of the films are both gastric films.

4. The laminated film of claim 2, wherein one side outermost film and the other side outermost film of the films are both enteric films.

5. The laminated film of claim 1, wherein the first and second poorly water soluble entrapped materials each independently comprise at least one selected from an active pharmaceutical ingredient (API) and a functional food ingredient.

* * * * *